United States Patent [19]
Kilen

[11] 3,961,522
[45] June 8, 1976

[54] APPARATUS FOR RECORDING DISCONTINUITIES

[76] Inventor: Joseph-Bernard Leon Kilen, rue Fernand Huet, 72, B.4920 Embourg, Belgium

[22] Filed: May 21, 1974

[21] Appl. No.: 472,036

[30] Foreign Application Priority Data
June 6, 1973  Belgium .................................. 44191

[52] U.S. Cl. ................................................. 73/67
[51] Int. Cl.² ......................................... G01N 29/04
[58] Field of Search ................. 73/67, 67.5 R, 67.7, 73/67.8 R, 67.8 S, 67.9, 71.5 US

[56] References Cited
UNITED STATES PATENTS

| | | | |
|---|---|---|---|
| 3,287,963 | 11/1966 | Stanya et al. ......................... | 73/67.9 |
| 3,416,364 | 12/1968 | Wycherly et al. ................. | 73/67.8 S |
| 3,555,889 | 1/1971 | Weighart ............................. | 73/67.9 |
| 3,677,073 | 7/1972 | Morgan ................................ | 73/67.9 |

Primary Examiner—Richard C. Queisser
Assistant Examiner—Stephen A. Kreitman
Attorney, Agent, or Firm—Young & Thompson

[57] ABSTRACT

In an apparatus for counting the faults contained in a given volume by reflection of ultrasonic waves from a transmitter there are provided pulse counters for registering any pulse constituting the video signal received by said counters which are preset to different actuation thresholds corresponding to different amplitude levels of the signals owing to the faults, said counters being subjected to a frequency divider and a time selector for avoiding counting the same fault several times and for authorizing counting during a time corresponding to the depth of the desired probing.

3 Claims, 1 Drawing Figure

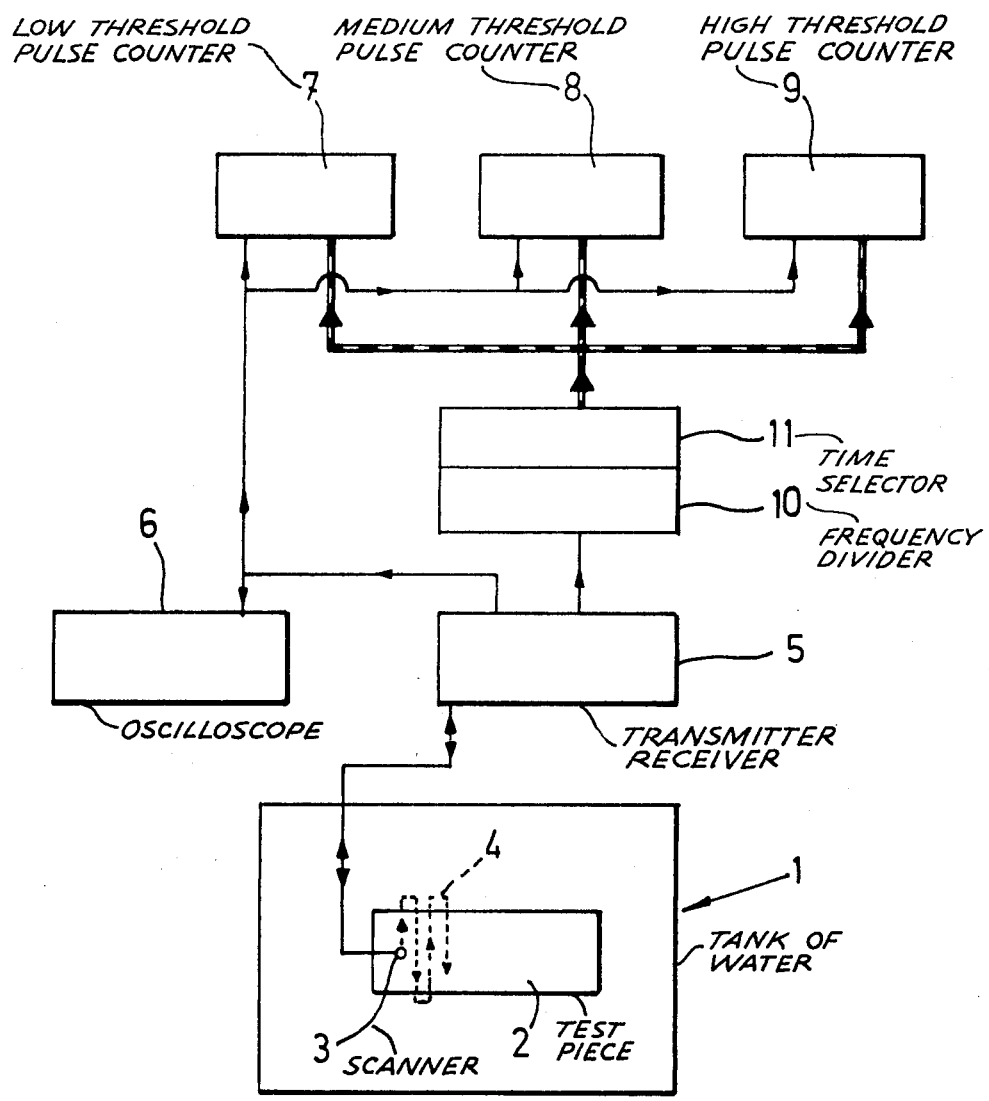

APPARATUS FOR RECORDING DISCONTINUITIES

The present invention relates to a device for counting faults contained in a given body by ultrasonic reflection and more particularly a device for counting the inclusions contained in a metal body.

It is known that ultrasonics may be used to count elements, articles, or products found in a given volume. In particular, metal or non-metal bodies are examined by probing by means of apparatus utilising the reflection of ultrasonic waves in order to determine the internal soundness of the body; this examination is particularly important if the body is to undergo subsequent operations such as deforming operations, for example shaping, wire-drawing, or forging, or if the optimum conditions of use are to be defined.

In order to carry out an examination with this type of apparatus, a test-piece is swept by a scanner emitting a beam of ultrasonic waves (focussed or not). When the ultrasonic waves strike faults, such as inclusions, they are reflected and provide echoes which are converted into electrical current pulses transmitted to a recording apparatus or to a counting means, such as a counter which functions if the amplitude of the signal reaches a given value or threshold. With present counting means, for a given position of the scanner at a given moment, if several faults are located in the path of the beam of ultrasonic waves, the counters (each having a different threshold) only function for the value of the signal corresponding to the first fault reaching the detection levels of the thresholds considered, so that the signals corresponding to any other faults encountered on the path of the beam do not have any action on the counters. The result is that all these "other faults" cannot be made compatible by the counters and the number of faults actually existing may be much higher than the number indicated by the counters, this being a source of error in judging the quality of the test-piece examined; in other words, this wrong evaluation of the number of faults leads to an incorrect judgment about the internal soundness of the body.

The present invention is concerned with the problem of providing a device which enables the sounding density of a given volume to be regulated at will; more particularly the device must enable the sounding density of a solid body to be regulated so that the number of faults detected is as near as possible to the number of faults which actually exist in the body.

In accordance with the invention, a device for counting the faults contained in a given volume (particularly inclusions in a metal casting) by reflection of the ultrasonic waves from a transmitter, comprises pulse counters which are capable of registering any pulse constituting the video signal which each receives as a whole, the said counters being preset to the actuation thresholds which are different from one to the other and corresponding to the different amplitude levels of the signals owing to the faults, the said counters being moreover subjected to the action of a frequency divider and a time selector so as to avoid counting the same fault several times whilst allowing a probing density which can be regulated according to the speed of exploration and so as to authorize the counting during a given time so as to correspond to the depth of the desired probing.

According to one embodiment, the frequency divider divides the recurring frequency of the ultrasonic transmitter and then acts on the time selector by releasing the counters.

According to a further embodiment, from the recurring frequency, the time selector selects the regulated time intervals according to the desired sounding depth and then the frequency divider divides the frequency of the signals corresponding to the selected time intervals so as to release the counters and permit counting.

Further features will be apparent from the following description of the accompanying drawing in which the sole FIGURE is a circuit diagram of one embodiment of apparatus according to the invention, given by way of example only.

The diagram includes only those parts which are useful for understanding the invention, and these are shown diagrammatically.

A tank 1 contains water in which is immersed a body 2 to be examined, for example a prismatic steel bar.

A scanner 3 is moved over the body 2 at a given exploration speed and follows a given course 4, for example zig-zag; this scanner, which advances at a speed of 50 mm/s, is supplied by an ultrasonic transmitter-receiver assembly 5 at a given ultrasonic frequency and at a given pulse repetition frequency, for example 400 pulses per second; this scanner 3 is adjusted so that the beam of ultrasonic waves which it emits has its focal point located on the longitudinal medial axis of the body 2. The ultrasonic waves of the beam encounter various discontinuities such as the faces defining the body and the inclusions; these discontinuities modify the propagation of the ultrasonic waves and give rise to reflections or echoes which are converted into pulses or electrical signals by the scanner 3 and are all received by the transmitter-receiver 5, which provides a video signal appearing on an oscilloscope 6. All the electric signals are supplied to each of three regulated pulse counters 7, 8, 9, each having a different command or response threshold; in other words, each counter is regulated for a given threshold which is peculiar to it and receives all the pulses resulting from the reflection of the ultrasonic waves.

The transmitter-receiver assembly 5 is connected to a frequency divider 10 which divides the frequency by a given factor, which is a sub-multiple of the pulse recurrence frequency. Thus, for example, if the frequency divider divides by 16 and the recurrence frequency of the apparatus 5 is 400, the result is 25 counts per second, which gives a count every 2 mm when the speed of the scanner is 50 mm/s. This frequency divider 10 then issues a periodic signal to a time selector 11 which releases the counters 7, 8, 9 for a predetermined time; these counters 7, 8, 9 are able to count only the pulses which they receive for a given period corresponding to a given sounding depth.

It is thus apparent that the frequency divider 10 enables the number of soundings to be varied along a given path of the scanner, i.e. to vary the density of the soundings, whilst the time selector enables the depth of the soundings to be varied so that they may be limited to a part of the thickness of the casting.

The pulse counters 7, 8, 9 are regulated according to the different respective operating thresholds, as mentioned above. Thus, for example, the counter 7 is regulated for the lowest threshold, i.e. it counts all the signals whose amplitude exceeds the lowest value, previously selected to correspond to the smallest faults to be counted; this counter thus counts all the faults, the smallest, medium-sized, and largest faults. The counter 8 is regulated for a higher operating threshold and counts all the signals whose amplitude exceeds a previously selected average value to correspond to the faults of an average size to be counted; thus this counter 8 counts all the medium-sized faults and the largest faults. The third counter 9 is regulated for an even higher operating threshold and counts only the signals whose amplitude exceeds a selected value to correspond to the most serious faults. From the difference between the different values indicated by the counters, it is easy to deduce the number of small, medium-sized, and large faults, i.e. it is possible to learn the number of faults included in each range.

The apparatus described is advantageous because, when examining a body, it enables the number of faults to be evaluated with a high degree of accuracy and to make the approximation as near as possible to the faults actually present, by increasing the number of counters; furthermore, it is possible to obtain a representation of the distribution of the faults according to their importance and to establish a representative quotation of the soundness or purity of the body.

The invention is not restricted to the embodiment described and it is possible to make certain modifications without departing from its scope as defined in the claims. Thus the frequency divider and the time selector may be reversed without affecting the result; the apparatus may comprise a greater or smaller number or counters; the oscilloscope may be omitted; the ultrasonic apparatus may comprise a transmitter and receiver which may or may not be separated; the apparatus according to the invention may be generally used to detect, count, and classify the discontinuities in any given volume and more particularly internal defects in a metal casting or plastics body.

What I claim is:

1. An ultrasonic non-destructive testing apparatus for detecting and counting discontinuities in a given volume and particularly inclusions in a piece, comprising an ultrasonic waves transmitter directing ultrasonic waves into said given volume at a given pulse repetition frequency, pulse counters capable of registering all the pulses constituting the video signal entirely received by each of said pulse counters, said pulse counters being each preset to a different actuation threshold, a frequency divider for dividing the pulse repetition frequency to vary the sounding density along the path of the scanner, and a time selector combined with said divider to allow each of said counters to count during a determined time corresponding to the depth of the desired probing all the signals whose amplitude exceeds the actuation threshold of the associated said counter.

2. An apparatus as claimed in claim 1, in which said frequency divider controls said time selector and said time selector releases said counters for a predetermined time.

3. An apparatus as claimed in claim 1, in which there are three said counters.

* * * * *